US009893886B2

(12) United States Patent
Tercero

(10) Patent No.: US 9,893,886 B2
(45) Date of Patent: Feb. 13, 2018

(54) COMMUNICATION DEVICE

(71) Applicant: DENSO CORPORATION, Kariya, Aichi-pref. (JP)

(72) Inventor: Carlos Tercero, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

(21) Appl. No.: 15/520,188

(22) PCT Filed: Oct. 19, 2015

(86) PCT No.: PCT/JP2015/005255
§ 371 (c)(1),
(2) Date: Apr. 19, 2017

(87) PCT Pub. No.: WO2016/067549
PCT Pub. Date: May 6, 2016

(65) Prior Publication Data
US 2017/0317825 A1    Nov. 2, 2017

(30) Foreign Application Priority Data
Oct. 28, 2014 (JP) .................................. 2014-219346

(51) Int. Cl.
*B60R 25/24* (2013.01)
*H04L 9/10* (2006.01)
(Continued)

(52) U.S. Cl.
CPC ................ *H04L 9/10* (2013.01); *B60R 25/24* (2013.01); *G01B 11/25* (2013.01);
(Continued)

(58) Field of Classification Search
CPC .............................. B60R 25/24; B60R 25/248
(Continued)

(56) References Cited

U.S. PATENT DOCUMENTS 6,850,148 B2 * 2/2005 Masudaya ............... B60R 25/24
340/5.61
7,546,571 B2   6/2009 Mankin et al.
(Continued)

FOREIGN PATENT DOCUMENTS

JP    2003013644 A    1/2003
JP    2006512515 A    4/2006
(Continued)

*Primary Examiner* — Kevin Kim
(74) *Attorney, Agent, or Firm* — Harness, Dickey & Pierce, P.L.C.

(57) ABSTRACT

A communication device includes a communication control unit generating a communication signal to be transmitted to an external source and an encryption unit connected to the communication control unit through a wiring. The communication control unit stores a predetermined communication signal indicative of a predetermined message and a target duration required for from a transmission of the predetermined communication signal to a reception of the same from the encryption unit. The communication control unit further counts an actual duration taken from the transmission of the predetermined communication signal to the reception of the same from the encryption unit. When the actual duration is longer than the target duration, the communication control unit determines that a fraudulent circuit is inserted into the wiring for fraudulently acting on the communication signal.

11 Claims, 3 Drawing Sheets

(51) Int. Cl.
*H04L 9/32* (2006.01)
*G07C 9/00* (2006.01)
*G01B 11/25* (2006.01)
*G01B 11/30* (2006.01)
*G01N 21/89* (2006.01)

(52) U.S. Cl.
CPC ............ *G07C 9/00309* (2013.01); *H04L 9/32* (2013.01); *G01B 11/306* (2013.01); *G01N 21/8901* (2013.01); *G07C 2009/00388* (2013.01); *G07C 2209/08* (2013.01)

(58) Field of Classification Search
USPC ..................................... 340/5.72, 5.61, 5.64
See application file for complete search history.

(56) References Cited

U.S. PATENT DOCUMENTS

| | | |
|---|---|---|
| 8,370,117 B2 | 2/2013 | Sims, Jr. et al. |
| 2003/0001723 A1 | 1/2003 | Masudaya |
| 2004/0083374 A1* | 4/2004 | Sugawara ............... B60R 25/24 |
| | | 713/189 |
| 2005/0041813 A1* | 2/2005 | Forest .................... B60R 25/24 |
| | | 380/262 |
| 2006/0164209 A1 | 7/2006 | De Zeeuw |
| 2009/0228118 A1 | 9/2009 | Von Schwertfuehrer et al. |
| 2015/0022332 A1* | 1/2015 | Lin ......................... B60R 25/20 |
| | | 340/426.1 |

FOREIGN PATENT DOCUMENTS

| | | |
|---|---|---|
| JP | 2007532369 A | 11/2007 |
| JP | 2012175518 A | 9/2012 |
| WO | WO-2005088561 A2 | 9/2005 |

\* cited by examiner

COMMUNICATION DEVICE

CROSS REFERENCE TO RELATED APPLICATIONS

This application is a U.S. National Phase Application under 35 U.S.C. 371 of International Application No. PCT/JP2015/005255 filed on Oct. 19, 2015 and published in Japanese as WO 2016/067549 A1 on May 6, 2016. This application is based on and claims the benefit of priority from Japanese Patent Application No. 2014-219346 filed on Oct. 28, 2014. The entire disclosures of all of the above applications are incorporated herein by reference.

TECHNICAL FIELD

The present disclosure relates to a communication device that performs a communication of encrypted data.

BACKGROUND ART

For example, Patent Literature 1 discloses a passive entry system. The system counts an elapsed time from a transmission of a request signal from a vehicle-mounted transceiver to a reception of an answer signal by the transceiver from a mobile transceiver, and locks or unlocks vehicle doors only when a value of counted time falls within an effective value of counted time. In the passive entry of Patent Literature 1, when a repeater is interposed between the vehicle-mounted transceiver and the mobile transceiver to perform a communication, the value of counted elapsed time exceeds the effective value of counted time due to a delay caused by the repeater. For that reason, with the configuration of Patent Literature 1, a vehicle theft by a method known as relay attack, which uses the repeater, can be prevented.

PRIOR ART LITERATURE

Patent Literature

Patent Literature 1: JP 2003-13644 A

SUMMARY OF INVENTION

The theft technique by a malicious third party is not limited to the relay attack using the repeater as described above.

For example, a cryptographic technique is usually used in the communication between the vehicle-mounted transceiver and the mobile transceiver. For that reason, each of the vehicle-mounted transceiver and the mobile transceiver needs to include an encryption and decryption circuit for encrypting a transmission signal and decrypting a received signal. The encryption and decryption circuit may be provided independently from a communication circuit that performs the communication in a hardware fashion. In that case, the communication circuit and the encryption and decryption circuit are connected to each other through a wiring.

In the above example, when the malicious third party succeeds in inserting of a fraudulent circuit into the wiring connecting the communication circuit to the encryption and decryption circuit, the fraudulent circuit is interposed between the communication circuit, and the encryption and decryption circuit. Thus, the fraudulent circuit is capable of performing illegal operation such as eavesdropping of transmitted and received signals and rewriting of transmitted and received signals. As a result, for example, unlocking of the vehicle doors or the like may be illegally performed, and the vehicle may be stolen.

In view of the foregoing difficulties, it is an object of the present disclosure to provide a communication device which is capable of reliably detecting a fraudulent circuit inserted into a wiring when the communication devices employs a configuration in which a communication control unit is connected with an encryption unit (decryption unit) via the wiring.

According to a first aspect of the present disclosure, a communication device includes a communication control unit and an encryption unit. The communication control unit generates a communication signal to be transmitted to an external source and transmits the communication signal. The encryption unit is connected to the communication control unit through a wiring. The encryption unit receives the communication signal from the communication control unit, encrypts the communication signal that is received, and then, returns the communication signal that is encrypted to the communication control unit. The communication control unit uses the communication signal encrypted by the encryption unit as the communication signal to be transmitted to the external source. The communication control unit includes a storage unit and a measurement unit. The storage unit stores a predetermined communication signal indicative of a predetermined message and a target duration required for from a transmission of the predetermined communication signal to the encryption unit until a reception of the predetermined communication signal that is encrypted from the encryption unit. The measurement unit counts an actual duration taken from the transmission of the predetermined communication signal to the encryption unit until the reception of the predetermined communication signal after the predetermined communication signal is encrypted and returned by the encryption unit. When the actual duration counted by the measurement unit is longer than the target duration, the communication control unit determines that a fraudulent circuit is inserted into the wiring for fraudulently acting on the communication signal.

As described above, the predetermined communication signal indicative of the predetermined message is stored in the storage unit, and the communication control unit transmits the predetermined communication signal indicative of the predetermined message to the encryption unit. Upon receiving the predetermined communication signal indicative of the predetermined message, the encryption unit encrypts the received predetermined communication signal and then returns the encrypted predetermined communication signal to the communication control unit. In this configuration, the communication control unit counts the actual duration required for from the transmission of the predetermined communication signal indicative of the predetermined message until the return of the communication signal with the user of a measurement unit. The target duration is a duration required for from the transmission of the predetermined communication signal indicative of the predetermined message to the encryption unit until the return of the predetermined communication signal, and is preliminarily stored in the storage unit. Thus, with the comparison of the actually measured duration with the target duration, it can be determined whether the encryption takes a normal duration or a duration longer than the normal duration to perform the communication between the communication control unit and the encryption unit. When the communication takes a duration longer than the normal duration, there is a high possibility that a circuit that performs some process on the communication signal is interposed between the communication control unit and the encryption unit. For that reason, when the duration actually measured is longer than the target duration, the communication control unit considers that the fraudulent circuit is inserted into the wiring for fraudulently acting on the communication signal. In this way, even when the fraudulent circuit is inserted into the wiring, the fraudulent circuit can be reliably detected.

According to a second aspect of the present disclosure, a communication device includes a communication control unit and a decryption unit. The communication control unit (130) receives a communication signal that is encrypted from an external source. The decryption unit (134) is connected to the communication control unit through a wiring. The decryption unit receives the communication signal that is encrypted from the communication control unit, decrypts the communication signal that is received, and then, returns the communication signal that is decrypted to the communication control unit. The communication control unit includes a storage unit and a measurement unit. The storage unit (132) stores a predetermined communication signal, which is encrypted and indicative of a predetermined message, and a target duration required for from a transmission of the predetermined communication signal indicative of the predetermined message to the decryption unit until a reception of the communication signal that is decrypted from the decryption unit. The measurement unit (S120, S130, S140) counts an actual duration taken from the transmission of the predetermined communication signal to the decryption unit until the reception of the predetermined communication signal after the predetermined communication signal is decrypted and returned by the decryption unit. When the actual duration counted by the measurement unit is longer than the target duration, the communication control unit determines that a fraudulent circuit is inserted into the wiring for fraudulently acting on the communication signal.

In the communication device according to the second aspect, as in the communication device according to the first aspect, even if the fraudulent circuit is inserted into the wiring, the fraudulent circuit can be reliably detected.

BRIEF DESCRIPTION OF DRAWINGS

The above and other objects, features and advantages of the present disclosure will become more apparent from the following detailed description made with reference to the accompanying drawings. In the drawings.

EMBODIMENTS FOR CARRYING OUT INVENTION

An embodiment of the present disclosure will be described with reference to the drawings. In the present embodiment, an example in which a communication device according to the present disclosure is applied to an electronic key system that can lock or unlock doors of a vehicle and start an engine without the use of a mechanical key will be described.

Figure 1:
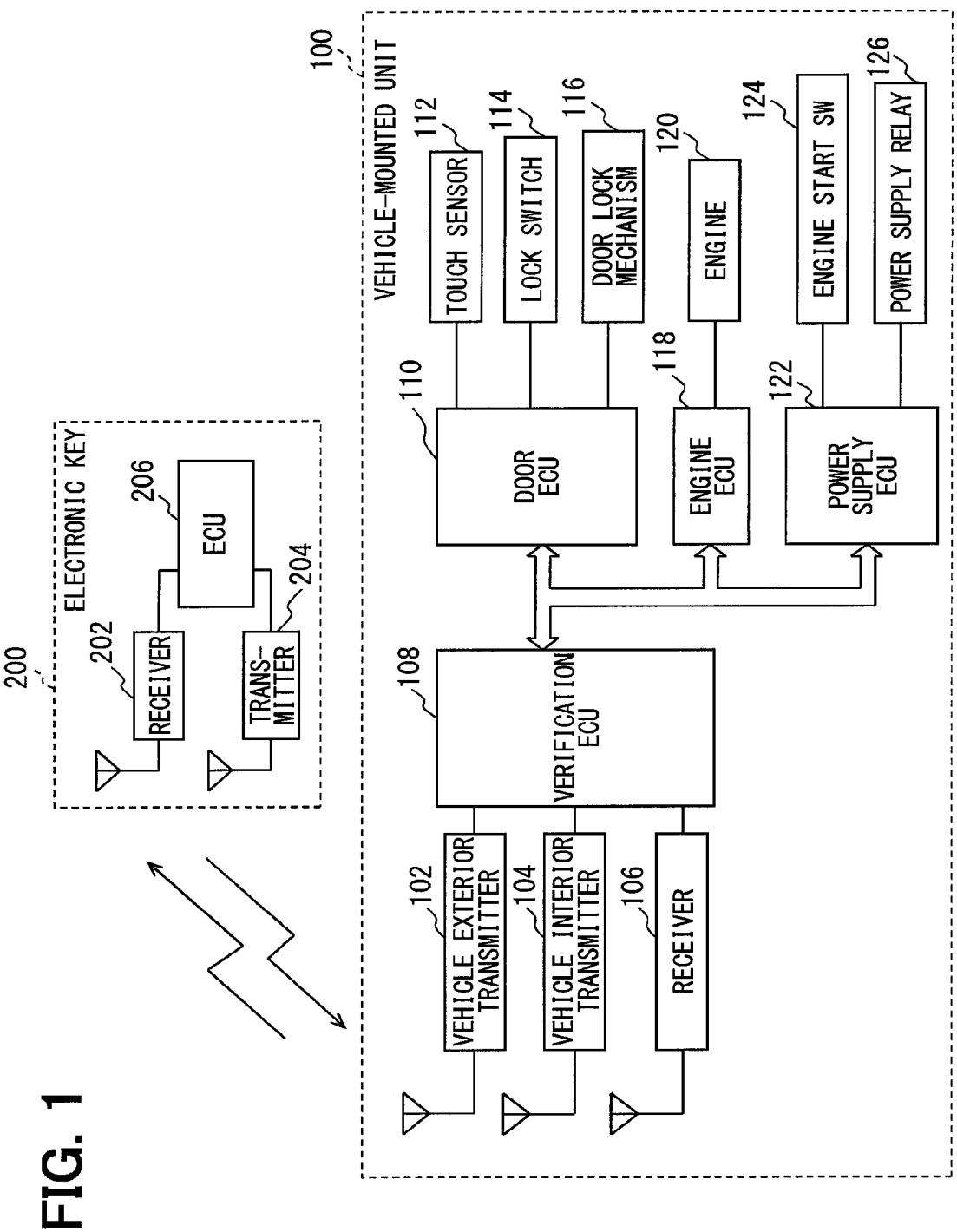
FIG. 1 is a diagram illustrating a configuration of an electronic key system employing a communication device according to the present disclosure.

FIG. 1 is a configuration diagram illustrating a configuration of an electronic key system. The electronic key system in the present embodiment performs a so-called smart entry function and an engine start function with the use of a wireless bidirectional communication between a vehicle-mounted unit 100 and an electronic key 200.

As illustrated in FIG. 1, an electronic key system according to the present embodiment includes the vehicle-mounted unit 100 mounted in a vehicle (not shown) and the electronic key 200 carried by a user. First, a configuration and a function of the vehicle-mounted unit 100 will be described.

The vehicle-mounted unit 100 includes a vehicle exterior transmitter 102 and a vehicle interior transmitter 104. Each of the transmitters 102 and 104 transmits a request signal for detecting the electronic key 200 according to a transmission instruction from a verification ECU 108. In FIG. 1, one vehicle exterior transmitter 102 and one vehicle interior transmitter 104 are illustrated. Alternatively, multiple vehicle exterior transmitters 102 and multiple vehicle interior transmitters 104 may be provided to the vehicle.

Also, as illustrated in FIG. 1, the vehicle-mounted unit 100 includes a receiver 106. The receiver 106 is installed at a predetermined position in internal portion of the vehicle, and receives an answer signal including a specified ID code. The answer signal is replied from the electronic key 200 that has received the request signal. Then, the receiver 106 outputs the received answer signal to the verification ECU 108.

The verification ECU 108 is a general purpose computer having a CPU, a memory, and so on. The verification ECU 108 executes a bidirectional communication process for communicating with the electronic key 200. The verification ECU 108 also executes a verification process to the ID code included in the answer signal received from the electronic key 200. The verification ECU 108 executes these process by executing a program stored in the memory in advance. The verification ECU 108 is connected to an in-vehicle LAN. The in-vehicle LAN is connected with a door ECU 110, an engine ECU 118, a power supply ECU 122, and so on.

The door ECU 110 drives a door lock mechanism 116 installed in each door of the vehicle to lock or unlock the door, and outputs, to the verification ECU 108, a detection signal from a switch or a sensor equipped to each door of the vehicle. In FIG. 1, although only one set of the door ECU 110 and the components associated with the door ECU 110 are illustrated. Alternatively, multiple sets are provided in correspondence with the multiple doors of the vehicle.

For example, FIG. 1 illustrates a touch sensor 112 as a sensor equipped to each door of the vehicle. For example, the touch sensor 112 is disposed inside of each door handle of the vehicle. When the touch sensor 112 detects that a user who carries the electronic key 200 touches the door handle, the door ECU 110 outputs a door handle operation detection signal to the verification ECU 108. Upon receiving the door handle operation detection signal, the verification ECU 108 outputs a door unlock instruction signal to the door ECU 110. The door ECU 110 drives the door lock mechanism 116 to unlock the door on the basis of the unlocking instruction signal.

When the verification ECU 108 determines that a verification (vehicle exterior verification) result of the ID code shows verification success, the verification ECU 108 instructs the door ECU 110 to activate the touch sensor 112 by supplying power. Herein, the verification of the ID code is carried out through the bidirectional communication that is performed by the vehicle exterior transmitter 102. As a result, a state of the electronic key 200 is set to a unlock standby state in which a touch operation is detectable when the user carrying the electronic key 200 touches the door handle.

FIG. 1 illustrates a lock switch 114 as a switch equipped to each door of the vehicle. The lock switch 114 is equipped to each door handle or attached to a portion in the vicinity of each door handle. When the user operates the lock switch 114, the door ECU 110 outputs a lock switch operation signal to the verification ECU 108. Upon receiving the lock switch operation signal, the verification ECU 108 outputs a lock instruction signal to the door ECU 110 on the condition that the vehicle exterior verification is succeeded. The door ECU 110 drives the door lock mechanism 116 to lock the door on the basis of the lock instruction signal. In this way, the smart entry function (smart door unlock and smart door lock) is provided by the electronic key system.

When the vehicle interior verification is succeeded through the bidirectional communication using the vehicle interior transmitter 104, in order to prevent the electronic key 200 from being left and locked in the vehicle compartment, the verification ECU 108 does not output the lock instruction signal to the door ECU 110 even though the verification ECU 108 receives the lock switch operation signal.

The power supply ECU 122 controls a power supply to various electrical components disposed in the internal portion of the vehicle. The power supply ECU 122 is connected with an engine start switch 124 that is operated by a user when starting or stopping an engine (not illustrated). In addition, although not shown, the power supply ECU 122 is connected with a shift position sensor that detects a position of a shift lever, and is connected with a brake pedal switch that detects a depression of a brake pedal. When the engine start switch 124 is operated in a state where the shift lever is at a parking position and the brake pedal is depressed, the power supply ECU 122 confirms an ID verification result output from the verification ECU 108. When the vehicle interior verification is succeeded, the verification ECU 108 notifies the power supply ECU 122 of this fact. Then, in order to start the power supply to the various electrical components, the power supply ECU 122 turns on a power supply relay 126.

In order to control the operation state of the engine corresponding to the driver's accelerator pedal operation, the engine ECU 118 controls an ignition time of the engine, a fuel injection quantity, and so on. Upon turning on the power supply relay 126, the power supply ECU 122 outputs a start signal to the engine ECU 118. The engine ECU 118 that has received the start signal confirms the ID verification result from the verification ECU 108. When the engine ECU 118 confirms that the vehicle interior verification is succeeded in the verification ECU 108, the engine ECU 118 starts the engine 120. In this way, the engine start function is achieved in the electronic key system.

Next, a configuration and a function of the electronic key 200 will be described. As illustrated in FIG. 1, the electronic key 200 includes a receiver 202, a transmitter 204, and an electronic key ECU 206. The electronic key 200 operates with a power supply from a battery which is not shown.

The receiver 202 receives the request signals transmitted from the transmitters 102 and 104 of the vehicle-mounted unit 100. Upon receiving the request signal, the receiver 202 outputs the request signal to the electronic key ECU 206. Upon receiving the request signal from the receiver 202, the electronic key ECU 206 generates the answer signal including the ID code of the electronic key 200, and controls the transmitter 204 to transmit the answer signal. In this way, the bidirectional wireless communication is performed between the vehicle-mounted unit 100 and the electronic key 200.

Figure 2:
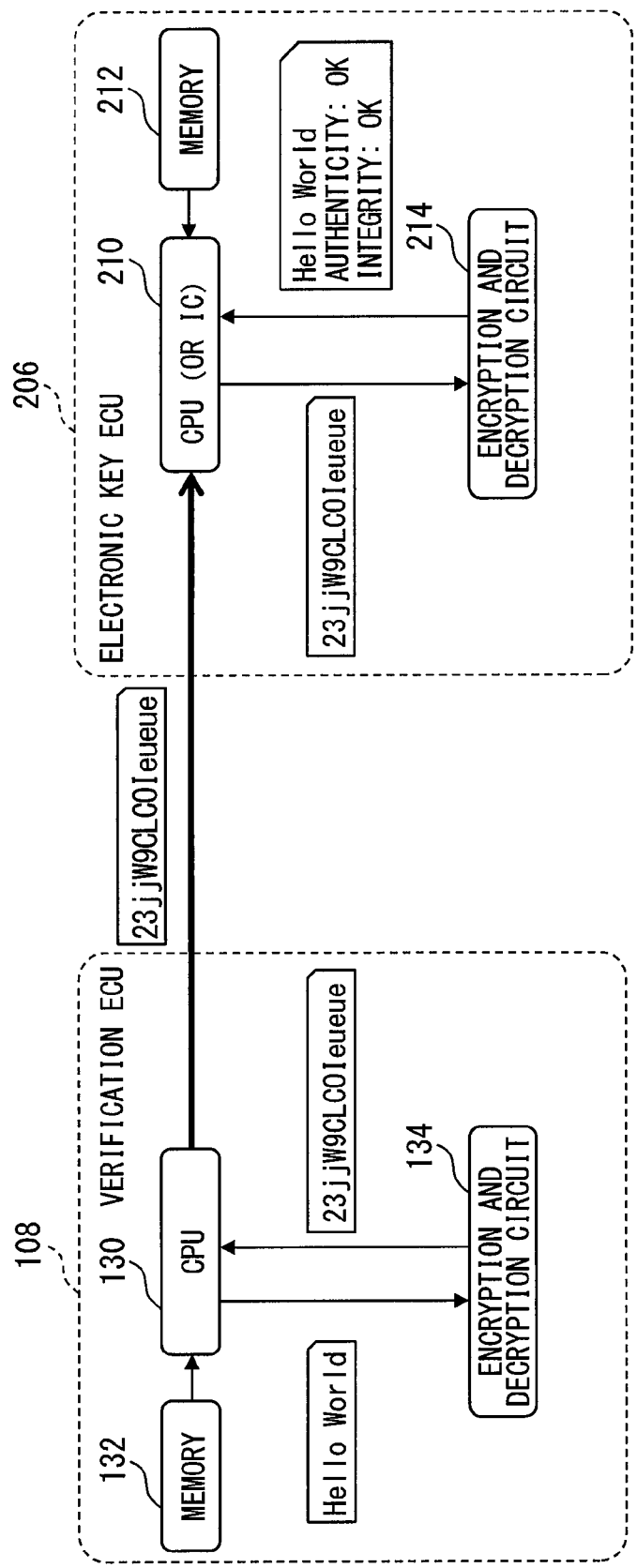
FIG. 2 is a diagram illustrating a detailed configuration of a verification ECU of a vehicle-mounted unit and an electronic key ECU of an electronic key.

In the above-described example, when the communication is performed between the vehicle-mounted unit 100 and the electronic key 200, since the ID code necessary to ensure security is included in a communication signal, the verification ECU 108 encrypts the communication signal, and then transmits the encrypted communication signal to the electronic key 200. When the electronic key 200 transmits the communication signal as a reply to the verification ECU 108, the electronic key 200 encrypts the communication signal and then transmits the encrypted communication signal to the vehicle-mounted unit 100. For that reason, as illustrated in FIG. 2, the verification ECU 108 includes an encryption and decryption circuit 134 for encrypting and decrypting the communication signal. Likewise, the electronic key ECU 206 includes an encryption and decryption circuit 214 for encrypting and decrypting the communication signal. In FIG. 2, the verification ECU 108 of the vehicle-mounted unit 100 and the electronic key ECU 206 of the electronic key 200 are mainly illustrated, and an illustration of the other configurations is omitted. In addition, the encryption and decryption circuits 134 and 214 may encrypt all of the communication signals or parts of the communication signals to be communicated between the vehicle-mounted unit 100 and the electronic key 200.

As illustrated in FIG. 2, the verification ECU 108 of the vehicle-mounted unit 100 includes a CPU 130 and a rewritable nonvolatile memory 132. The CPU 130 executes a predetermined program stored in the nonvolatile memory 132, to thereby execute, for example, the generation of the communication signal, the encryption of the communication signal by the encryption and decryption circuit 134, and a transmission process of the encrypted communication signal, and transmit the communication signal to the electronic key 200. At the time of receiving the communication signal, the CPU 130 executes the reception of the encrypted communication signal, the decryption of the communication signal by the encryption and decryption circuit 134, and a reception process of the decrypted communication signal. The memory 132 functions as a storage unit in the present disclosure.

For example, as a software structure in the CPU 130, a structure under a known AUTOSAR is employed, and an encryption service manager can be developed in a service layer of basic software. For example, an SPI driver is developed in a microcontroller abstraction layer (MCAL) in the basic software, as a result of which the encryption service manager can be configured to be communicable with the encryption and decryption circuit 134 through the SPI driver. With the employment of the above configuration, since the encryption service manager does not depend on hardware configuration, for example, the CPU, an influence caused by a change of the CPU can be minimized.

Similar to the verification ECU 108 of the vehicle-mounted unit 100, as illustrated in FIG. 2, the electronic key ECU 206 of the electronic key 200 includes a CPU (or IC) 210 and a rewritable nonvolatile memory 212. The CPU 210 executes a predetermined program, to thereby execute a transmission and reception process of the communication signal and an encryption or decryption process of the communication signal.

Any of known encrypting techniques may be used for the encryption process to be performed by the encryption and decryption circuits 134 and 214. For example, the encryption and decryption circuits 134 and 214 can perform a digital signature as the encryption process. In the digital signature, a digest is generated, with the use of a hash function, from the communication signal indicative of a message to be transmitted, and the generated digest is encrypted with a secret key. With the transmission of the encrypted signal together with the communication signal, falsification of the communication signal and the like can be detected. In other words, when receiving the encrypted signal, the encryption and decryption circuits 134 and 214 verify the digital signature. More specifically, the digest is generated from the communication signal, and the encrypted signal is decrypted with the use of a public key for decrypting the digest. Then, it is checked whether the generated digest is identical to the decrypted digest, or not. In this case, when the two digests are identical to each other, it can be verified that the communication signal has not been falsified, and the integrity of the communication signal can be determined. Furthermore, it can be verified that the communication signal is signed by the secret key paired with the public key, and the authenticity of the communication signal can be determined.

Further, the encryption and decryption circuits 134 and 214 may also perform the encryption process to the communication signal indicative of a message to be transmitted. In the example shown in FIG. 2, the digital signature is performed and the encryption process is performed to the communication signal. Referring to FIG. 2, a description will be given about a procedure of encryption and decryption when transmitting the communication signal indicative of a predetermined message ("Hello World") from the vehicle-mounted unit 100 to the electronic key 200.

The communication signal indicative of the predetermined message ("Hello World") to be transmitted by the CPU 130 is first generated, and the communication signal is transmitted to the encryption and decryption circuit 134. The encryption and decryption circuit 134 performs the digital signature on the received communication signal and encrypts the communication signal. In FIG. 2, the digital signature and the encrypted communication signal are indicated as "23jjW9CLCOIeueue". The encrypted communication signal and digital signature are returned to the CPU 130. The CPU 130 transmits the encrypted communication signal and digital signature received from the encryption and decryption circuit 134.

Upon receiving the encrypted communication signal and digital signature, the CPU 210 of the electronic key ECU 206 transmits the received encrypted communication signal and digital signature to the encryption and decryption circuit 214. The encryption and decryption circuit 214 decrypts the encrypted communication signal and generates the digest of the communication signal. In addition, the encryption and decryption circuit 214 decrypts the digital signature and restores the digest. Then, it is determined whether generated digest is identical to the restored digest or not. When the two digests are identical to each other, the authenticity and the integrity of the communication signal are determined to be secured. The encryption and decryption circuit 214 returns the decrypted communication signal ("Hello World") indicative of the predetermined message and the determination results of the authenticity and the integrity to the CPU 210. In the present embodiment, the security of the bidirectional communication between the vehicle-mounted unit 100 and the electronic key 200 is ensured with the use of the encryption of the communication signal, the digital signature, and so on.

In the above example, the integrity of the communication signal is secured by the digital signature. Alternatively, a message authentication code (MAC) may be used instead of the digital signature. The message authentication code is calculated through a predetermined MAC algorithm with the common key and the communication signal including the message to be authenticated as an input. In the above example, the digital signature is performed together with the encryption of the communication signal. Alternatively, any one of the digital signature or the encryption process may be performed.

In the present embodiment, as illustrated in FIG. 2, in the verification ECU 108 of the vehicle-mounted unit 100 and the electronic key ECU 206 of the electronic key 200, the hardware configurations of respective encryption and decryption circuits 134 and 214 are independent from the CPUs 130 and 210, and are connected to the CPUs 130 and 210 through respective wirings.

When the hardware configuration of the CPUs 130 and 210 are independent from the hardware configuration of the encryption and decryption circuits 134 and 214 and the CPUs 130 and 210 are connected to the encryption and decryption circuits 134 and 214 through respective wirings, there is a possibility that a malicious third party may insert a fraudulent circuit into the wiring connecting the CPUs 130, 210 to the encryption and decryption circuit 134, 214. When such a fraudulent circuit is actually inserted, the fraudulent circuit is interposed between the CPU 130, 210 and the encryption and decryption circuit 134, 214, to thereby enable unauthorized operation such as eavesdropping of the communication signal and rewriting of the communication signal or the like. As a result, for example, unlocking of the vehicle doors or the like is illegally performed, and the vehicle may be stolen.

In the communication device according to the present embodiment, when the fraudulent circuit is inserted into the wiring between the CPU 130, 210 and the encryption and decryption circuit 134, 214, the fraudulent circuit can be reliably detected in the CPU 130, 210. Hereinafter, the process to be performed by each CPU 130, 210 for detecting the fraudulent circuit will be described in detail with reference to a flowchart of FIG. 3. In the following description, a process executed by the CPU 130 of the verification ECU 108 in the vehicle-mounted unit 100 will be described as an example. It is desirable that the same process is executed by the CPU 210 of the electronic key ECU 206 in the electronic key 200.

Figure 3:
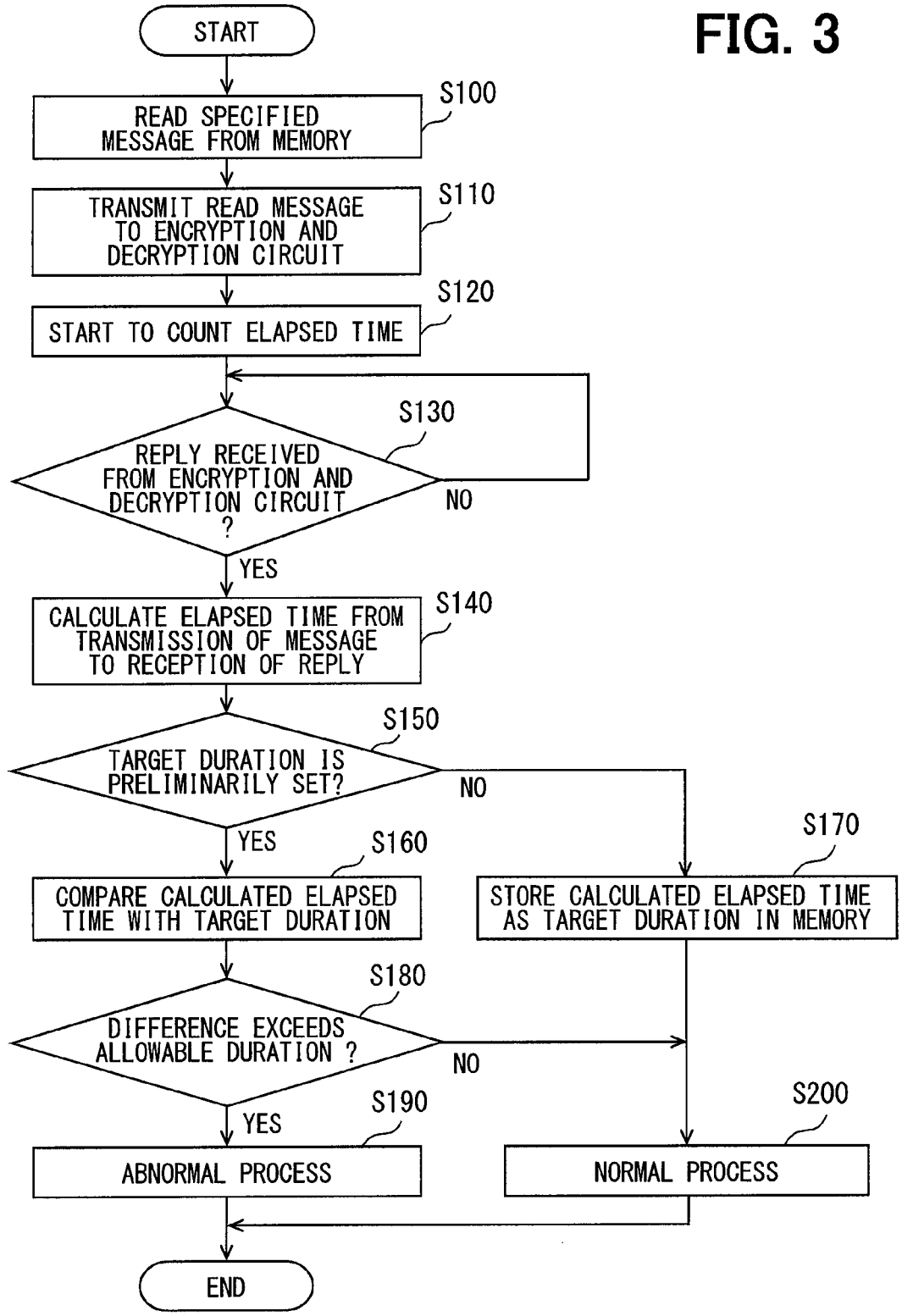
FIG. 3 is a flowchart illustrating process executed by a CPU for detecting a fraudulent circuit.

The process illustrated in the flowchart of FIG. 3 is executed when a predetermined start condition is satisfied. As the satisfaction of the predetermined start condition, a turn-on of the power supply or a transmission and reception of a series of communication signals is needed between the vehicle-mounted unit 100 and the electronic key 200. As a result, it is possible to determine whether the fraudulent circuit is inserted, or not, periodically or before the communication is actually performed.

In step S100 of the flowchart in FIG. 3, a specified message is read from the memory 132. The specified message is prepared in advance and stored in the memory 132 for the purpose of detecting whether the fraudulent circuit is inserted into the wiring between the CPU 130 and the encryption and decryption circuit 134.

In subsequent step S110, the CPU 130 transmits the predetermined communication signal indicative of the specified message that is read out to the encryption and decryption circuit 134. Then, in step S120, the CPU 130 activates an internal timer, and starts to count an elapsed time from the transmission of the predetermined communication signal indicative of the specified message. That is, the CPU 130 functions as a measurement unit. In step S130, the CPU 130 determines whether the encrypted communication signal and the digital signature from the encryption and decryption circuit 134 is received or not. When it is determined that the encrypted communication signal has not yet been received, the CPU 130 waits for the reception. On the other hand, when it is determined that the encrypted communication signal is received, the flow proceeds to step S140, and calculates the elapsed time from the transmission of the predetermined communication signal indicative of the specified message to the reception of the encrypted communication signal and digital signature. In S140, the elapsed time is calculated on the basis of the count value of an internal timer.

In subsequent step S150, it is determined whether the target duration has been set or not. That is, it is determined that whether the target duration is stored in the memory 132. In the present embodiment, when the vehicle-mounted unit 100 is initially powered, an actual duration required for the encryption of the predetermined communication signal indicative of the specified message and execution of the digital signature is counted, and set as the target duration in the vehicle-mounted unit 100. For that reason, in step S150, it is determined whether the target duration is stored and set in the memory 132. The vehicle-mounted unit 100 is first powered at a final stage of a manufacturing process of the vehicle-mounted unit 100. For that reason, in the first power on of the vehicle-mounted unit 100, it is considered that no fraudulent circuit is inserted into the wiring between the CPU 130 and the encryption and decryption circuit 134.

When it is determined in step S150 that the target duration has not yet been set, the process proceeds to step S170, and the elapsed time calculated in step S140 is set as the target duration and stored in the memory 132. On the other hand, when it is determined that the target duration has been set in step S150, the process proceeds to step S160, and the elapsed time calculated in step S140 is compared with the target duration. In step S180, it is determined whether a result of the comparison in step S160 indicates a difference between the elapsed time and the target duration exceeds an allowable duration or not. In the determination process, when it is determined that the difference between the elapsed time and the target duration falls within the allowable duration, the process proceeds to step S200, and normal process is continuously executed as usual. In other words, the CPU 130 executes the generation of the communication signal, the transmission of the communication signal to the encryption and decryption circuit 134, the reception of the communication signal from the encryption and decryption circuit 134, and the communication process of the encrypted communication signal and the digital signature with the electronic key 200. On the other hand, in step S180, when it is determined that the difference between the elapsed time and the target duration exceeds the allowable duration, the process proceeds to step S190.

When the fraudulent circuit is inserted into the wiring between the CPU 130 and the encryption and the decryption circuit 134, the communication signal passes through the fraudulent circuit. A delay occurs in the communication between the CPU 130 and the encryption and decryption circuit 134 due to process such as eavesdropping or falsification of the communication signal in the fraudulent circuit. Therefore, when the fraudulent circuit is inserted, it is determined that the difference between the elapsed time and the target duration exceeds the allowable duration in step S180. In that case, the process proceeds to step S190. In S190, it is considered that the communication has an abnormality, and an abnormal process is executed. As the abnormal process, for example, a process may be executed to stop the CPU 130 transmitting the communication signal to the encryption and decryption circuit 134, and then, inform the user of the vehicle that there is a possibility that the fraudulent circuit is inserted. Thus, the CPU 130 functions as an annunciation unit.

According to the communication device of the present embodiment, when the fraudulent circuit is inserted between the CPU 130 and the encryption and decryption circuit 134, the CPU 130 can detect the fraudulent circuit. Further, when the fraudulent circuit is detected, with the execution of the above-mentioned abnormal process, the communication signal can be prevented from being eavesdropped or falsified by the fraudulent circuit.

The preferred embodiment of the present disclosure has been described above, but this disclosure is not limited to the above-mentioned embodiment at all and can be modified without departing from the gist of this disclosure.

For example, in the embodiment described above, the example in which the communication device of the present disclosure is applied to the communication between the vehicle-mounted unit 100 and the electronic key 200 has been described. Alternatively, the communication device of the present disclosure may be applied to the communication among the ECUs included in the vehicle-mounted unit 100. As described above, communication is also performed among the verification ECU 108, the door ECU 110, the engine ECU, and the power supply ECU 122 for confirmation of the comparing result and so on. In this configuration, in order to conceal communication contents, it is conceivable to exchange the encrypted communication signals among the multiple ECUs in the vehicle-mounted unit 100. In that case, it is preferable that the communication device according to the present disclosure is applied to a configuration in which the CPU functioning as a communication control unit and the encryption and decryption circuit 134 functioning as an encryption unit and a decryption unit are independent from each other in a hardware fashion, and connected to each other by a wiring.

The application of the communication device according to the present disclosure is not limited to the electronic key system. When a wireless communication or a wired communication of the encrypted communication signal is performed, the communication device according to the present disclosure may also be applied to a configuration in which there is a need to prevent the communication signal from being eavesdropped or falsified by the fraudulent circuit.

In the embodiments described above, the CPU 130 reads the specified message from the nonvolatile memory 132, and compares the elapsed time required for from the transmission of the predetermined communication signal indicative of the specified message to the reception of the communication signal with the target duration, to thereby detect the fraudulent circuit. Alternatively, the CPU 130 may transmit the encrypted communication signal instead of the specified message, receive the communication signal decrypted by the encryption and decryption circuit 134, and compare the elapsed time required for from the transmission of the communication signal until the reception of the communication signal with the target duration. This is because the encryption and decryption circuit 134 has not only a function of encrypting the communication signal but also a function of decrypting the encrypted communication signal. With such a configuration, as in the embodiment described above, the insertion of the fraudulent circuit into the wiring between the CPU 130 and the encryption and decryption circuit 134 can be detected.

Further, in the embodiment described above, when the vehicle-mounted unit 100 is initially powered, the time actually required for from the transmission of the communication signal indicative of the specified message to the reception of the encrypted communication signal is set as the target duration. Alternatively, a target duration determined by experiments or by calculation can be stored in the memory 132 as the target duration together with the specified message in advance.

While the disclosure has been described with reference to preferred embodiments thereof, it is to be understood that the disclosure is not limited to the preferred embodiments and constructions. The disclosure is intended to cover various modification and equivalent arrangements. In addition, the various combinations and configurations, which are preferred, other combinations and configurations, including more, less or only a single element, are also within the spirit and scope of the disclosure.

The invention claimed is:

1. A communication device comprising:
a communication control unit generating a communication signal to be transmitted to an external source and transmitting the communication signal; and
an encryption unit connected to the communication control unit through a wiring, wherein the encryption unit receives the communication signal from the communication control unit, encrypts the communication signal that is received, and then, returns the communication signal that is encrypted to the communication control unit, the communication control unit uses the communication signal encrypted by the encryption unit as the communication signal to be transmitted to the external source, wherein
the communication control unit includes:
a storage unit storing a predetermined communication signal indicative of a predetermined message and a target duration required for from a transmission of the predetermined communication signal to the encryption unit until a reception of the predetermined communication signal that is encrypted from the encryption unit; and
a measurement unit counting an actual duration taken from the transmission of the predetermined communication signal to the encryption unit until the reception of the predetermined communication signal after the predetermined communication signal is encrypted and returned by the encryption unit, and
when the actual duration counted by the measurement unit is longer than the target duration, the communication control unit determines that a fraudulent circuit is inserted into the wiring for fraudulently acting on the communication signal.

2. The communication device according to claim 1, wherein
the communication control unit transmits the predetermined communication signal indicative of the predetermined message when a power supply is activated, and
the measurement unit counts the actual duration until the reception of the predetermined communication signal after the predetermined communication signal is encrypted and returned by the encryption unit.

3. The communication device according to claim 1, wherein
the communication control unit transmits the predetermined communication signal indicative of the predetermined message prior to a transmission of the communication signal to the encryption unit when a transmission of the communication signal to the external source is required, and
the measurement unit counts the actual duration until the reception of the predetermined communication signal after the predetermined communication signal is encrypted and returned by the encryption unit.

4. The communication device according to claim 1, wherein
the communication control unit stops an output of the communication signal to the encryption unit when determining that the fraudulent circuit is inserted into the wiring.

5. The communication device according to claim 1, further comprising
an annunciation unit performs an annunciation to a user when the communication control unit determines that the fraudulent circuit is inserted into the wiring.

6. The communication device according to claim 1, wherein,
under a condition that only the encryption unit is connected to the communication control unit through the wiring, the actual duration taken from the transmission of the predetermined communication signal indicative of the predetermined message until the reception of the predetermined communication signal from the encryption unit is set as the target duration and is stored in the storage unit.

7. A communication device comprising:
a communication control unit receiving a communication signal that is encrypted from an external source; and
a decryption unit connected to the communication control unit through a wiring, wherein the decryption unit receives the communication signal that is encrypted from the communication control unit, decrypts the communication signal that is received, and then, returns the communication signal that is decrypted to the communication control unit, wherein
the communication control unit includes:
a storage unit storing a predetermined communication signal, which is encrypted and indicative of a predetermined message, and a target duration required for from a transmission of the predetermined communication signal indicative of the predetermined message to the decryption unit until a reception of the communication signal that is decrypted from the decryption unit; and
a measurement unit counting an actual duration taken from the transmission of the predetermined communication signal to the decryption unit until the reception of the predetermined communication signal after the predetermined communication signal is decrypted and returned by the decryption unit, and
when the actual duration counted by the measurement unit is longer than the target duration, the communication control unit determines that a fraudulent circuit is inserted into the wiring for fraudulently acting on the communication signal.

8. The communication device according to claim 7, wherein
the communication control unit transmits the predetermined communication signal indicative of the predetermined message when a power supply is activated, and the measurement unit counts the actual duration until the reception of the predetermined communication signal after the predetermined communication signal is decrypted and returned by the decryption unit.

9. The communication device according to claim 7, wherein
the communication control unit stops an output of the communication signal to the decryption unit when determining that the fraudulent circuit is inserted into the wiring.

10. The communication device according to claim 7, further comprising
an annunciation unit performs an annunciation to a user when the communication control unit determines that the fraudulent circuit is inserted into the wiring.

11. The communication device according to claim 7, wherein
under a condition that only the decryption unit is connected to the communication control unit through the wiring, the actual duration taken from the transmission of the predetermined communication signal indicative of the predetermined message until the reception of the predetermined communication signal from the decryption unit is set as the target duration and is stored in the storage unit.

* * * * *